United States Patent
Lopez (10) Patent No.: US 9,474,896 B2
(45) Date of Patent: Oct. 25, 2016

(54) STRAIN RELIEVED LEAD ROUTING IN BURR HOLE PLUG FOR DEEP BRAIN STIMULATION

(75) Inventor: Thomas P. Lopez, Sunland, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 785 days.

(21) Appl. No.: 13/491,031

(22) Filed: Jun. 7, 2012

(65) Prior Publication Data

US 2012/0316628 A1    Dec. 13, 2012

Related U.S. Application Data

(60) Provisional application No. 61/494,820, filed on Jun. 8, 2011.

(51) Int. Cl.
*A61N 1/00* (2006.01)
*A61N 1/05* (2006.01)

(52) U.S. Cl.
CPC .............. *A61N 1/0539* (2013.01); *A61B 90/10* (2016.02); *A61B 2090/103* (2016.02); *A61B 2562/187* (2013.01); *A61N 1/0534* (2013.01)

(58) Field of Classification Search
CPC .................. A61B 2090/103; A61B 2562/187; A61B 90/10; A61N 1/0534; A61N 1/0539
USPC .......... 600/377, 378, 386; 604/175; 606/129, 606/130; 607/116, 139, 149
See application file for complete search history.

(56) References Cited

U.S. PATENT DOCUMENTS

| | | | |
|---|---|---|---|
| 6,845,267 B2 | 1/2005 | Harrison et al. | |
| 6,950,707 B2 | 9/2005 | Whitehurst | |
| 2009/0112327 A1* | 4/2009 | Lane et al. | 623/17.19 |
| 2009/0157157 A1* | 6/2009 | Schorn et al. | 607/149 |

* cited by examiner

*Primary Examiner* — William Levicky
*Assistant Examiner* — Lindsey G Hankins
(74) *Attorney, Agent, or Firm* — Lowe Graham Jones PLLC; Bruce E. Black (57) ABSTRACT

A method of performing a medical procedure comprises introducing a medical device through a cranial burr hole into the brain tissue, mounting a plug base around a cranial burr hole, securing the medical device within the aperture of the plug base, seating a proximal end of the medical device within a first groove of the plug base, such that the proximal end exits the aperture of the plug base through the first groove, looping the proximal end from the first groove to a second groove in the plug base, seating the proximal end within the second groove, such that the proximal end extends across the aperture of the plug base from the second groove, and seating the proximal end within a third groove of the plug base, such that the proximal end exits the plug base aperture through the third groove.

15 Claims, 11 Drawing Sheets

STRAIN RELIEVED LEAD ROUTING IN BURR HOLE PLUG FOR DEEP BRAIN STIMULATION

RELATED APPLICATION DATA

The present application claims the benefit under 35 U.S.C. §119 to U.S. provisional patent application Ser. No. 61/494,820, filed Jun. 8, 2011. The foregoing application is hereby incorporated by reference into the present application in its entirety.

FIELD OF THE INVENTION

The present inventions relate to apparatus for securing elongated medical devices, such as catheters or leads, within a cranial burr hole.

BACKGROUND OF THE INVENTION

Deep brain stimulation (DBS) and other related procedures involving implantation of electrical stimulation leads within the brain of a patient are increasingly used to treat disorders, such as Parkinson's disease, dystonia, essential tremor, seizure disorders, obesity, depression, restoration of motor control, and other debilitating diseases via electrical stimulation via stimulation of one or more target sites, including the ventrolateral thalamus, internal segment of globus pallidus, substantia nigra pars reticulate, subthalamic nucleus (STN), or external segment of globus pallidus. DBS has become a prominent treatment option for many disorders, because it is a safe, reversible alternative to lesioning. For example, DBS is the most frequently performed surgical procedure for the treatment of advanced Parkinson's Disease. There have been approximately 30,000 patients worldwide that have undergone DBS surgery. Consequently, there is a large population of patients who will benefit from advances in DBS treatment options.

During DBS procedures, at least one burr hole is meticulously cut through the patient's cranium so as not to damage the brain tissue below, a large stereotactic targeting apparatus is mounted to the patient's cranium, and a cannula is scrupulously positioned towards the target site in the brain. A stimulation lead is then introduced through the cannula, through the burr hole, and into the parenchyma of the brain, such that one or more electrodes located on the stimulation lead are strategically placed at a target site in the brain of the patient. Once the stimulation lead is properly positioned, the portion of the stimulation lead exiting the burr hole is subcutaneously routed underneath the patient's scalp to an implantable pulse generator (IPG) implanted in the patient at a site remote from the burr hole (e.g., the patient's shoulder or chest region). Further details discussing the treatment of diseases using DBS are disclosed in U.S. Pat. Nos. 6,845,267, 6,845,267, and 6,950,707, which are expressly incorporated herein by reference.

Significantly, it is crucial that proper location and maintenance of the stimulation lead position be accomplished in order to continuously achieve efficacious therapy. This is especially so with DBS applications, in which cases, the target site (or sites) that is intended for electrical stimulation is about the size of a pea and is located deep within the patient's brain. Thus, lead displacements of less than a millimeter may have a deleterious effect on the patient's therapy. Therefore, it is important that that the electrode(s) of the stimulation lead be accurately located at the target site and that such electrode(s) be securely maintained at the target site during and after implantation of the stimulation lead. In addition, it is important that the burr hole be sealed around the stimulation lead to prevent infection or leakage of cerebrospinal fluid.

Figure 1:
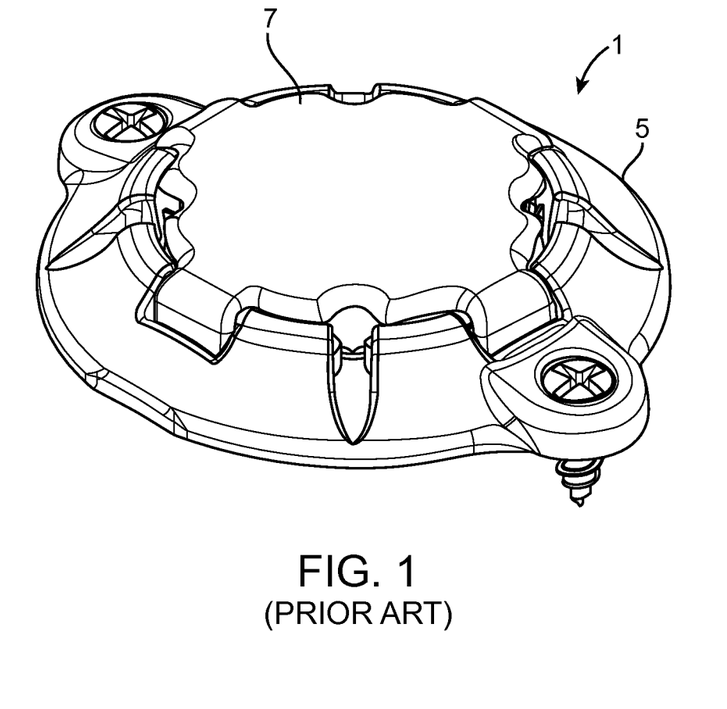
FIG. 1 is a perspective view of a prior art burr hole plug that can be used to secure a Deep Brain Stimulation (DBS) lead.
Figure 2:
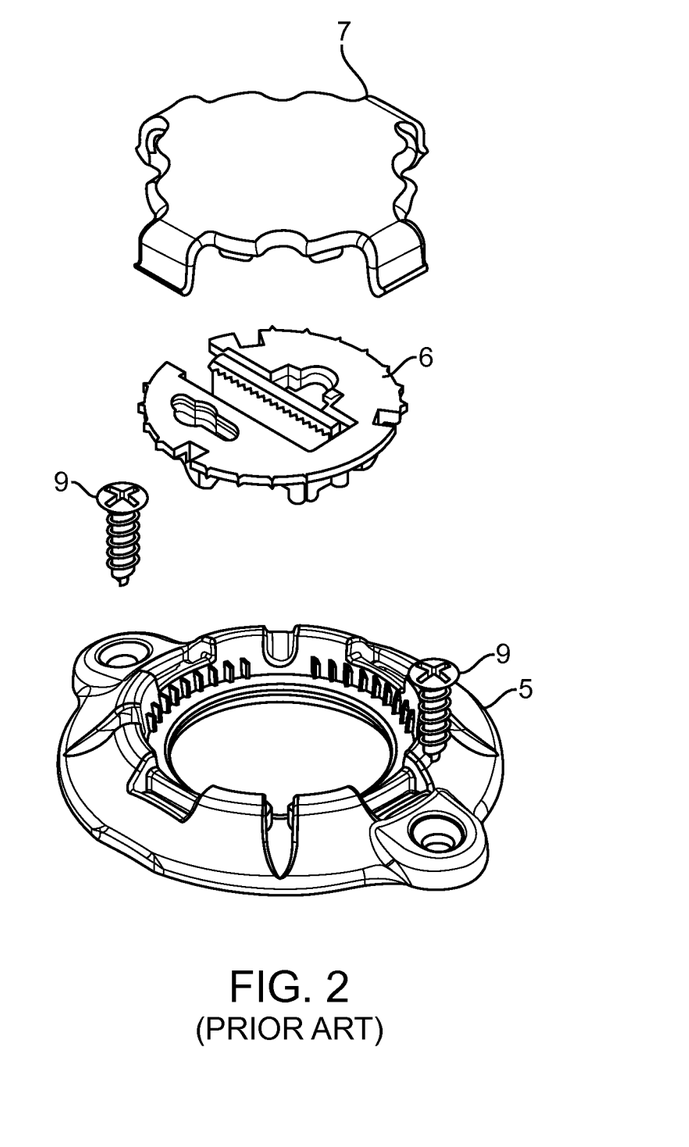
FIG. 2 is an exploded perspective view of the prior art burr hole plug of FIG. 1.
Figure 3:
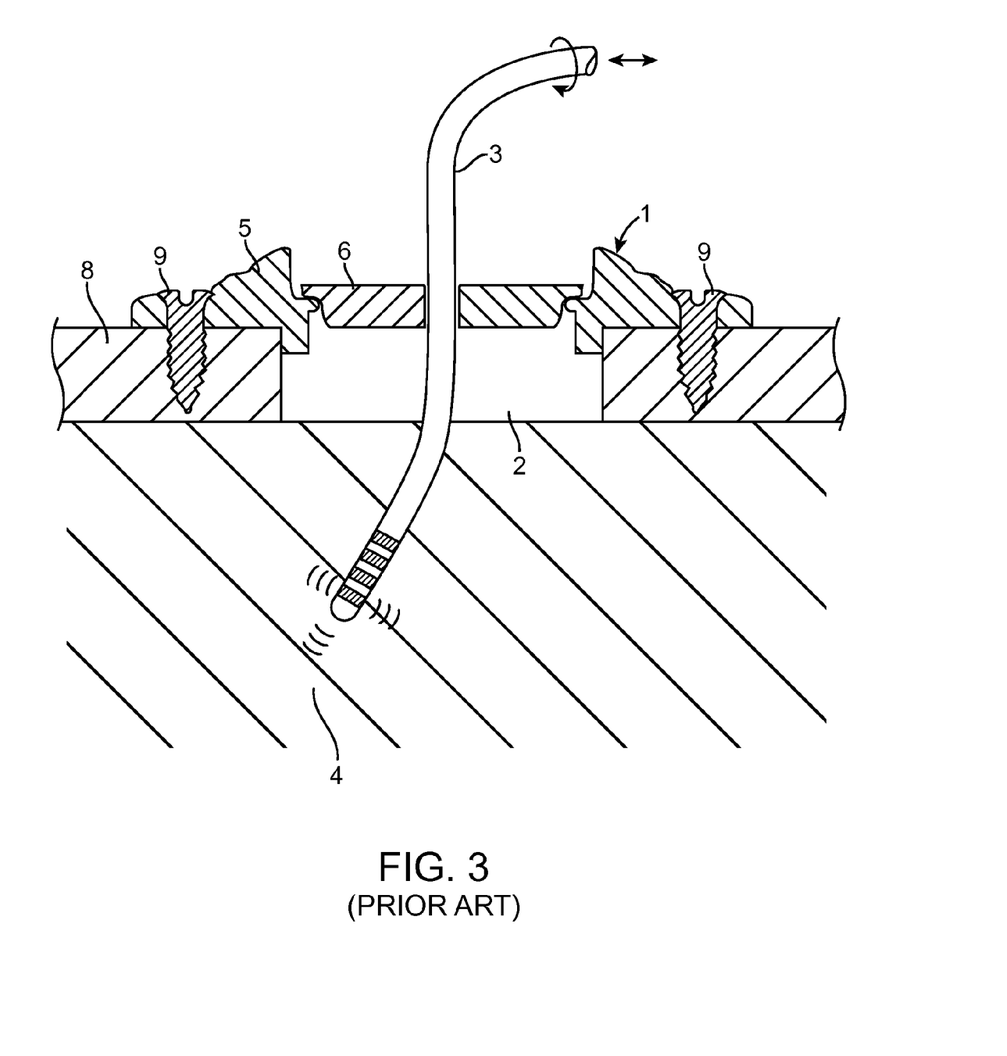
FIG. 3 is a cross-sectional view of the prior art burr hole plug of FIG. 1 used to secure a stimulation lead within a burr hole.

To address these issues, and with reference to FIGS. 1-3, a cranial burr hole plug 1, may be installed within the burr hole 2 during the implantation procedure to hold the stimulation lead 3 in place, thereby maintaining the relevant electrode(s) of the stimulation lead 3 at the target site within the brain 4 of the patient, as well as to seal the burr hole 2. As further shown in FIG. 2, the burr hole plug 1 may comprise a multitude of components, including a ring-shaped plug base 5, which is permanently mounted to the patient's cranium 8 using fasteners, such as screws 9, a retainer 6, which is mounted within the plug base 5 and is used to secure the lead 3 in place, and a cap 7, which can be installed onto the plug base 5 over the retainer 6 to permanently secure the stimulation lead 3, as well as to seal the burr hole 2. Further details regarding these types of burr hole plugs are disclosed in U.S. patent application Ser. No. 12/258,382, entitled "Burr Hole Plug With Self-Centering Tabs," which is expressly incorporated herein by reference.

Notably, any displacement of the portion of the stimulation lead 3 exiting the burr hole 2 will result in the translation of the electrodes positioned in the brain 4 relative to the target site, thereby requiring the stimulation lead 3 to be repositioned—a time-consuming process. Although the retainer 6 is designed to temporarily secure the stimulation lead 3 before the cap 7 is installed onto the plug base 5, the distal tip of the stimulation lead 3 may be prone to movement when the proximal end of the stimulation lead 3 is flexed, as shown in FIG. 3.

There, thus, remains a need to better secure a stimulation lead within a burr hole plug to prevent or minimize migration of the distal tip of the stimulation lead relative to the target site in the brain.

SUMMARY OF THE INVENTION

In accordance with the present inventions, a method of performing a medical procedure on a patient is provided. The method comprises introducing an elongated medical device (e.g., an electrical stimulation lead) through a cranial burr hole of the patient and into the brain tissue of the patient. The method further comprises mounting a plug base around a cranial burr hole, such that the medical device extends through an aperture of the plug base. In one method, the plug base is ring-shaped. The plug base has at least three grooves formed in a top surface thereof. In another method, the plug base has four grooves that are circumferentially spaced ninety degrees from each other. The grooves may extend along an axis that intersects a center of the aperture.

The method further comprises securing the medical device within the aperture of the plug base. In one method, a retainer is mounted within the aperture of the plug base and actuated to secure the medical device. The retainer may include a clamping mechanism, in which case, the retainer may be actuated by clamping the medical lead with the clamping mechanism to secure the medical device. The method further comprises seating a proximal end of the medical device within a first one of the grooves, such that the proximal end of the medical device exits the aperture of the plug base through the first groove. The medical device may be bent at an angle (e.g., ninety degree angle) relative to an axis of the burr hole prior to seating the medical device within the first groove. In one method, the medical device is secured within a slot formed in the retainer, and the first groove extends perpendicularly to the slot.

The method further comprises looping the proximal end of the medical device around an outer circumference of the plug base from the first groove to a second one of the grooves. In one method the first groove and the second groove are circumferentially spaced from each other by ninety degrees. The method further comprises seating the proximal end of the medical device within the second groove, such that the proximal end of the medical device extends across the aperture of the plug base from the second groove, and seating the proximal end of the medical device within a third one of the grooves, such that the proximal end of the medical device exits the aperture of the plug base through the third groove.

In one method the second groove and the third groove are circumferentially spaced from each other by ninety degrees. The proximal end of the medical device may be looped within the aperture of the plug base between the second groove and the third groove. An optional method further comprises mounting a cap to the plug base over the retainer, such that the proximal end of the medical device is secured between the plug base and the cap.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

Referring to FIGS. 4-8, one method of implanting a stimulation lead within a brain of a patient using a burr hole plug will now be described. Although the exemplary method is described in the context of the burr hole plug 1 and stimulation lead 3 previously described with respect to FIGS. 1-3, the method described herein can be used with other types of burr hole plugs and stimulation leads.

Figure 4:
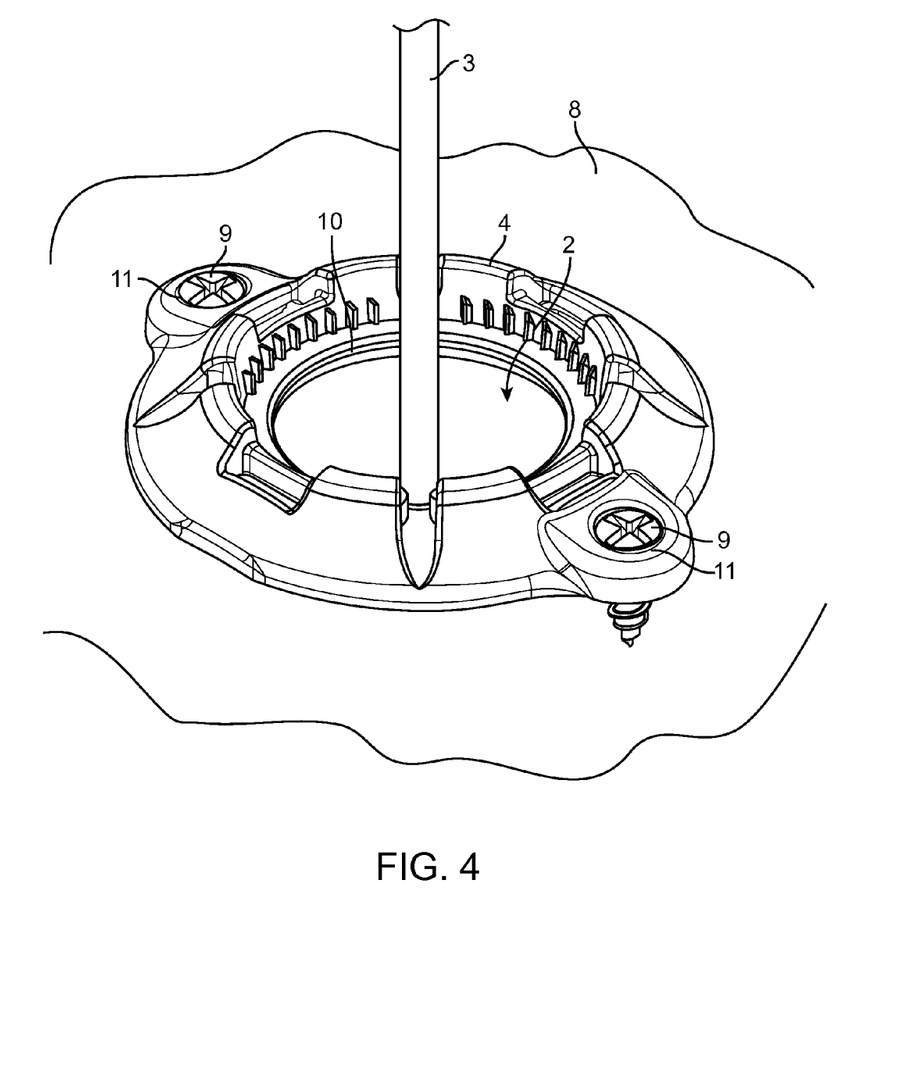
FIG. 4 is a perspective view showing a burr hole plug base mounted to a cranium and a stimulation lead extending from a burr hole.

Referring first to FIG. 4, the plug base 4 is placed on top of the cranium 8 of the patient, such that plug base 4 is disposed around the burr hole 2 formed in the cranium 8, effectively aligning an aperture 10 of the plug base 4 with the burr hole 2. The plug base 4 may have centering tabs or an annular flange (not shown) that can be disposed within the burr hole 2 to facilitate centering of the plug base 4 relative to the burr hole 2. The plug base 4 is then anchored to the cranium 8 using suitable fasteners, such as screws 9 introduced through screw holes 11 formed in the plug base 4.

Next, the stimulation lead 12 is introduced through the plug base aperture 10, through the burr hole 2, and into the brain tissue, such that the electrodes (not shown) of the stimulation lead 3 are adjacent the target site. In an alternative method, the plug base 4 may have a slot (not shown), in which case, the stimulation lead 3 may first be introduced through the burr hole 2, the stimulation lead 3 may then be laterally introduced within the slot of the plug base 4, and then the plug base 4 can then be disposed over and anchored to the cranium 8 in the same manner described above with respect to FIG. 4. In another alternative embodiment, the plug base 4 may be split into two sections, in which case, the stimulation lead 2 may first be introduced through the burr hole 2, the two sections of the plug base 4 may be mated together around the stimulation lead 2, and then the mated plug base 4 may be disposed over and anchored to the cranium 8 in the same manner described above with respect to FIG. 4. These alternative embodiments are described in U.S. patent application Ser. No. 12/258,382, which was previously incorporated herein by reference.

Figure 5:
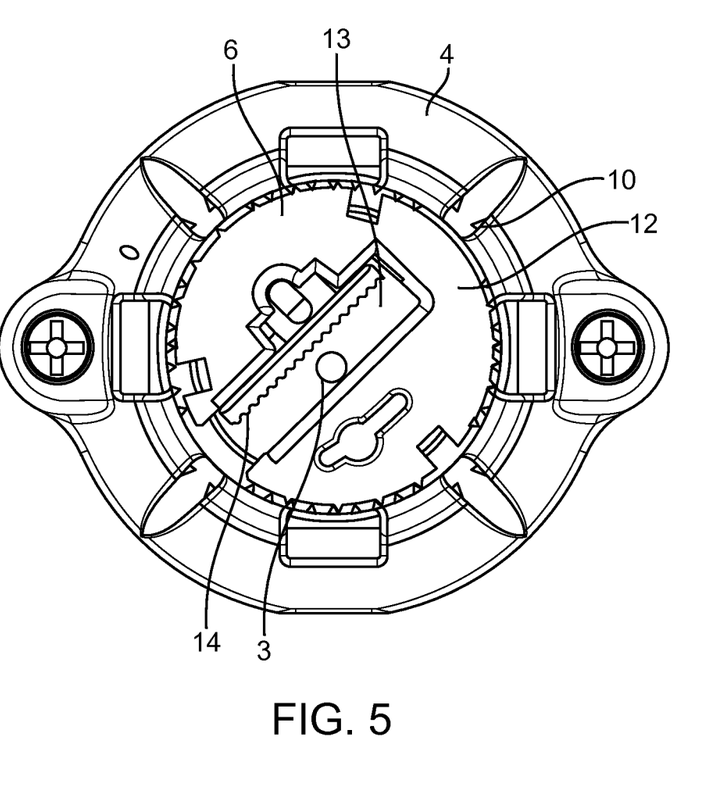
FIG. 5 is a top view of the burr hole plug base of FIG. 4 and a retainer mounted within the burr hole plug base.
Figure 6:
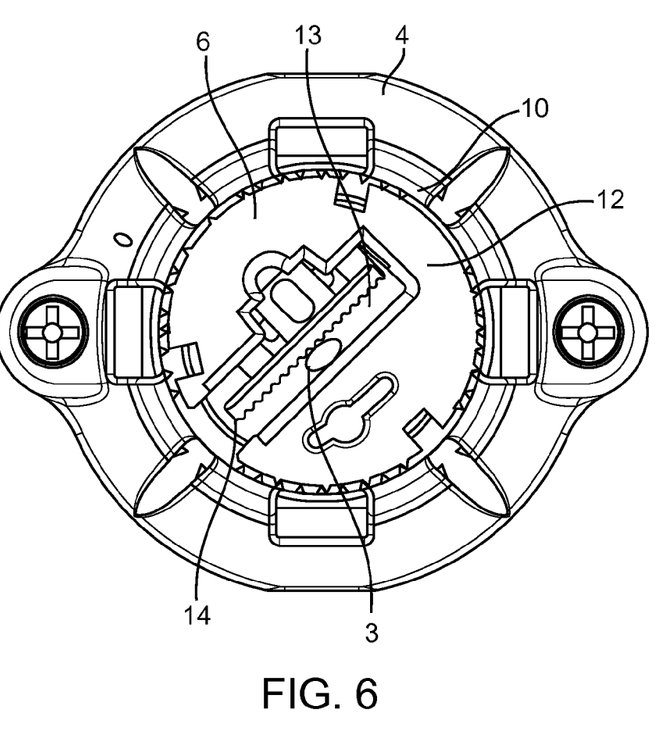
FIG. 6 is a top view of the burr hole plug base and retainer of FIG. 5, wherein the stimulation lead is secured within the retainer.

After the plug base 4 has been anchored to the cranium 8 and the stimulation lead 3 introduced through the burr hole 2 and properly located adjacent the target site, the retainer 6 is mounted within the plug base aperture 10, as illustrated in FIG. 5. Once the retainer 6 is firmly mounted within the plug base aperture 10, the retainer 6 may then be actuated to secure the stimulation lead 3 within the plug base aperture 10, as illustrated in FIG. 6. In the illustrated embodiment, the retainer 6 comprises a disk 12 having a slot 13 for laterally receiving the stimulation lead 3 and a clamping mechanism 14 that can be slid relative to a mating surface adjacent the slot 13 to frictionally clamp the received lead 3 therebetween. The clamping mechanism 14 may have one or more locking mechanisms that can engage or disengage complementary locking mechanisms on the disk 12 to prevent movement of the clamping mechanism 14. Further details discussing this type of retainer 6, as well as alternative embodiments of retainers, for securing the stimulation lead 3, are described in U.S. patent application Ser. No. 12/258,382, which was previously incorporated herein by reference.

Figure 7:
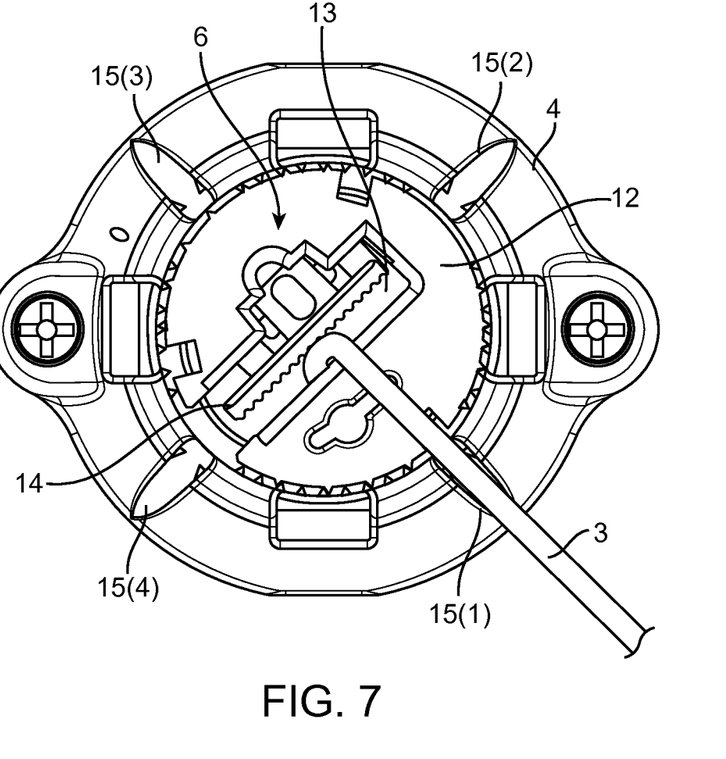
FIG. 7 is a top view of the burr hole plug base and retainer of FIG. 6, wherein the stimulation lead is shown bent down and seated within a first groove in the plug base.

After the stimulation lead 3 is secured within the plug base aperture 10, the proximal end of the stimulation lead 3 (i.e., the portion that extends from the retainer 6) is bent at an angle (in this case, perpendicular, i.e., 90 degrees) relative to a longitudinal axis of the burr hole 2, and then seated within one of four lead grooves 15(1)-15(4) formed in the top surface of the plug base 4, such that the proximal end of the stimulation lead 3 exits the aperture 10 through the groove 15(1), as shown in FIG. 7. In the illustrated embodiment, the four grooves 15 are circumferentially spaced ninety degrees from each other around the plug base 4. Furthermore, each groove 15 extends along an axis that intersects the center of the plug base aperture 10. In the preferred method, the particular groove 15 in which the stimulation lead 3 is seated is the one that extends along an axis that is perpendicular to the slot 14 of the retainer 6. To this end, prior to mounting within the plug base 4, the retainer 6 may be rotated within the plug base 4 to ensure that one of the grooves 15 is perpendicular to the slot 13.

Figure 8:
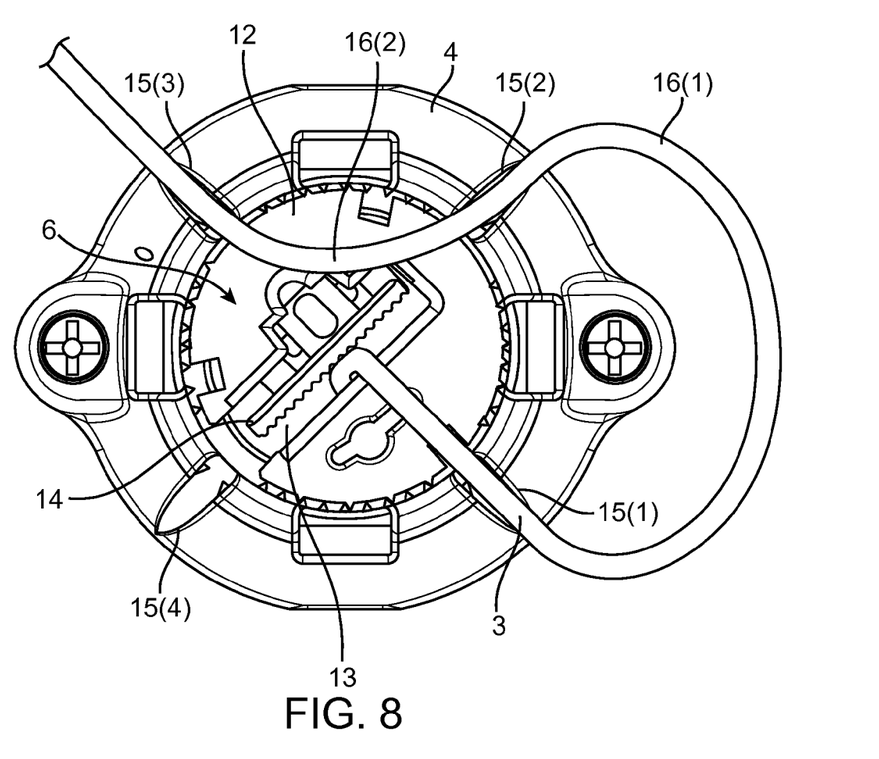
FIG. 8 is a top view showing one stimulation lead configuration formed on the burr hole plug base FIG. 6.

Next, the proximal end of the stimulation lead 3 is looped around the outer circumference of the plug base 4 from the first groove 15(1) to a second one of the grooves 15(2), seated within the second groove 15(2), such that the proximal end of the stimulation lead 3 extends across the plug base aperture 10 above the retainer 6 from the second groove 15(2), looped within the plug base aperture 10 between the second groove 15(2) and a third one of the grooves 15(3), and then seated within a third one of the grooves 15(3), such that the proximal end of the stimulation lead 3 exits the plug base aperture 10 through the third grove 15(3), as shown in FIG. 8.

In this manner, two strain relief loops 16 are formed in the proximal end of the stimulation lead 12 (a first strain relief loop 16(1) between the first groove 15(1) and the second groove 15(2), and a second strain relief loop 16(2) between the second groove 15(2) and the third groove 15(3)), which absorbs any inadvertent movement of the proximal end of the stimulation lead 12, thereby preventing, or at least minimizing, movement of the distal end of the stimulation lead 12.

Figure 9:
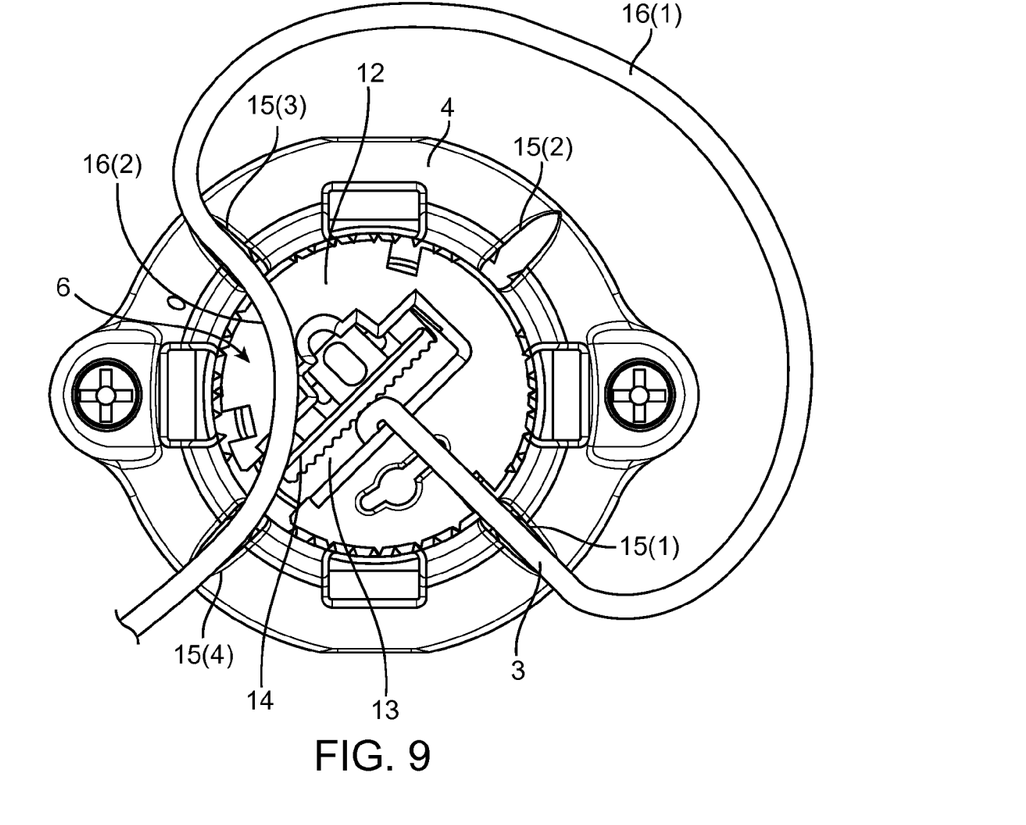
FIG. 9 is a top view showing another stimulation lead configuration formed on the burr hole plug base FIG. 6.
Figure 10:
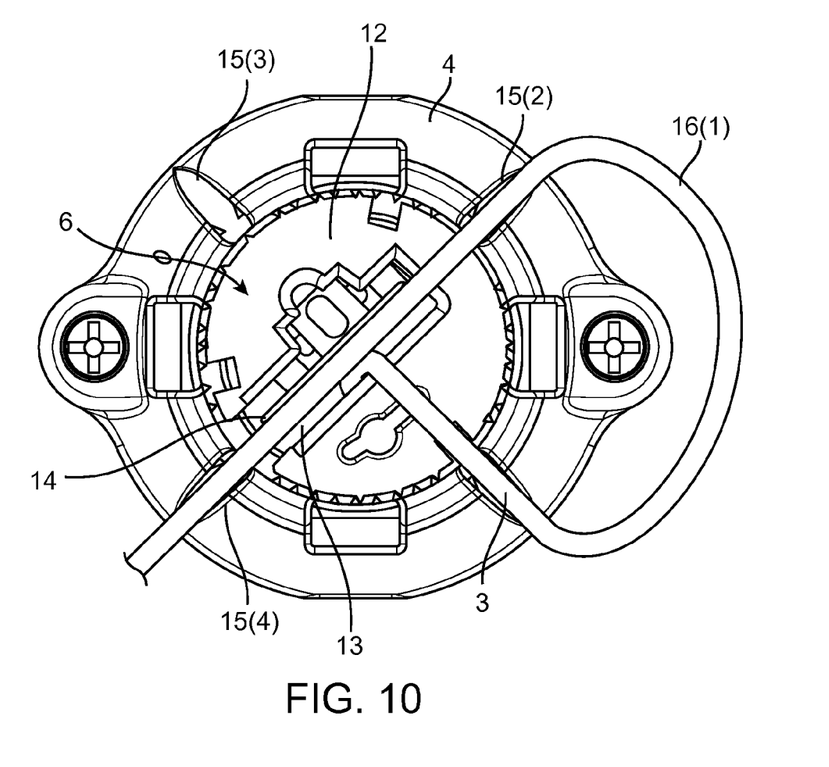
FIG. 10 is a top view showing still another stimulation lead configuration formed on the burr hole plug base FIG. 6.

Although the first strain relief loop 16(1) is shown as being formed between the first groove 15(1) and the second groove 15(2) in FIG. 8, it can be appreciated that the first strain relief loop 16(1) can be formed between the first groove 15(1) and the third groove 15(3) (or any oppositely disposed pair of grooves 15) by seating the proximal end of the stimulation lead 3 within the third groove 15(3) instead of the second groove 15(2), as shown in FIG. 9. Although two strain relief loops are shown in the configurations of FIGS. 8 and 9, it can be appreciated that one of the strain relief loops can be eliminated. For example, the proximal end of the stimulation 12 may be extended from the second groove 15(2) and seated within the fourth groove 15(4), as shown in FIG. 10. In either of the embodiments illustrated in FIGS. 8-10, the grooves 15 that are selected for seating the proximal end of the stimulation lead 3 are preferably such that proximal end of the stimulation lead 3 is on a more direct trajectory to the neurostimulator (not shown), thereby avoiding the need to route the stimulation lead 3 further around the burr hole plug 1.

Figure 11:
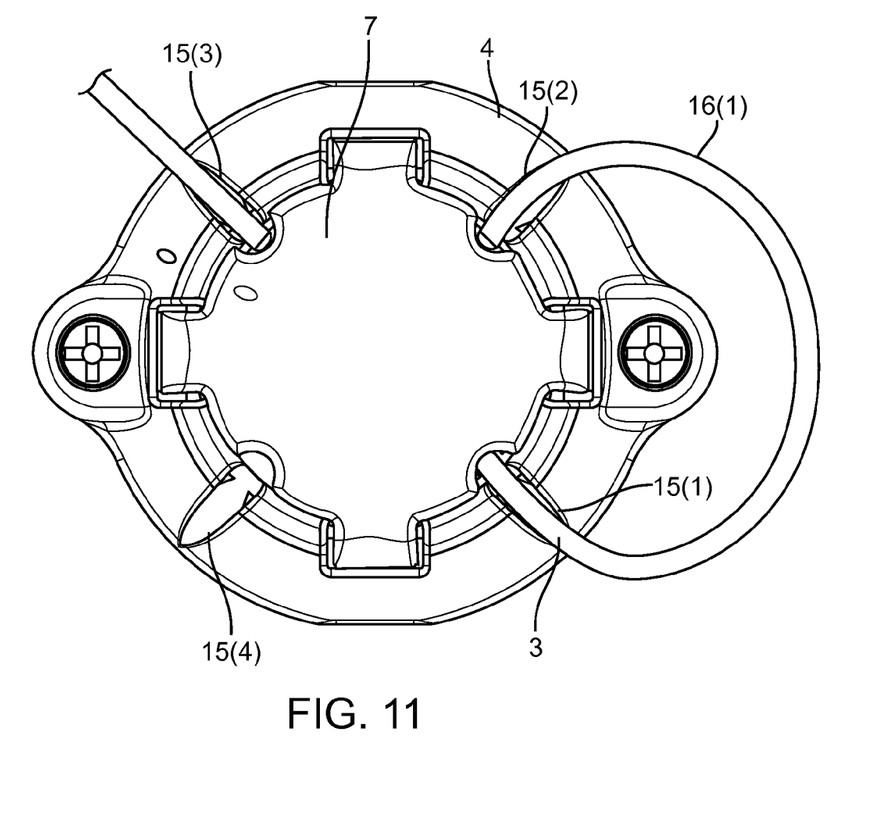
FIG. 11 is a top view showing the installation of the cap on the plug base.

Once the proximal end of the stimulation lead 3 is seated within the selected grooves 15 of the plug base 4, the cap 7 is mounted to the plug base 4 over the retainer 6, such that the stimulation lead 3 is secured between the plug base 4 and the cap 7, as illustrated in FIG. 11. In the illustrated embodiment, the cap 7 includes lead clamp grooves (not shown) that spatially correspond to the grooves 15 on the plug base 4, such that these grooves will capture and apply downward pressure to the proximal end of the stimulation lead 3 to frictionally secure the stimulation lead 3 within the selected grooves 15 of the plug base 4.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of performing a medical procedure on a patient, comprising:
   introducing an elongated medical device through a cranial burr hole of the patient and into the brain tissue of the patient;
   mounting a plug base around a cranial burr hole, such that the medical device extends through an aperture of the plug base, the plug base having at least three grooves formed in a top surface of the plug base;
   securing the medical device within the aperture of the plug base;
   seating a proximal end of the medical device within a first groove of the at least three grooves, such that the proximal end of the medical device exits the aperture of the plug base through the first groove;
   looping the proximal end of the medical device around an outer circumference of the plug base from the first groove to a second groove of the at least three grooves;
   seating the proximal end of the medical device within the second groove, such that the proximal end of the medical device extends across the aperture of the plug base from the second groove; and
   seating the proximal end of the medical device within a third groove of the at least three grooves, such that the proximal end of the medical device exits the aperture of the plug base through the third groove.

2. The method of claim 1, wherein the medical device is an electrical lead.

3. The method of claim 1, wherein the plug base is ring-shaped.

4. The method of claim 1, further comprising mounting a cap to the plug base, wherein the proximal end of the medical device is secured between the plug base and the cap.

5. The method of claim 4, further comprising looping the proximal end of the medical device within the aperture of the plug base between the second groove and the third groove.

6. The method of claim 1, further comprising bending the medical device at an angle relative to an axis of the burr hole prior to seating the medical device within the first groove.

7. The method of claim 6, wherein the angle is a ninety degree angle.

8. The method of claim 1, further comprising:
   mounting a retainer within the aperture of the plug base; and
   actuating the retainer to secure the medical device.

9. The method of claim 8, wherein the medical device is secured within a slot formed in the retainer, and the first groove extends perpendicularly to the slot.

10. The method of claim 8, wherein the retainer includes a clamping mechanism, and the retainer is actuated by clamping the medical lead with the clamping mechanism to secure the medical device.

11. The method of claim 8, wherein the proximal end of the medical device is seated within the first groove after actuating the retainer to secure the medical device.

12. The method of claim 1, wherein the first groove and the second groove are circumferentially spaced ninety degrees from each other around the plug base.

13. The method of claim 1, wherein the second groove and the third groove are circumferentially spaced ninety degrees from each other around the plug base.

14. The method of claim 1, wherein each of the at least three grooves extends along an axis that intersects a center of the aperture.

15. The method of claim 1, wherein the at least three grooves comprises four grooves that are circumferentially spaced ninety degrees from each other.

* * * * *